US00PP21983P2

(12) United States Plant Patent
Lee

(10) Patent No.: US PP21,983 P2
(45) Date of Patent: Jun. 21, 2011

(54) ***GARDENIA JASMINOIDES* PLANT NAMED 'LEEONE'**

(50) Latin Name: *Gardenia jasminoides*
Varietal Denomination: Leeone

(75) Inventor: Robert Edward Lee, Independence, LA (US)

(73) Assignee: Plant Development Services, Inc., Loxley, AL (US)

( * ) Notice: Subject to any disclaimer, the term of this patent is extended or adjusted under 35 U.S.C. 154(b) by 0 days.

(21) Appl. No.: 12/654,710

(22) Filed: Dec. 30, 2009

(51) Int. Cl.
*A01H 5/00* (2006.01)

(52) U.S. Cl. ..... Plt./255

(58) Field of Classification Search ..... Plt./255
See application file for complete search history.

*Primary Examiner* — Susan B McCormick Ewoldt

(74) *Attorney, Agent, or Firm* — Breiner & Breiner, L.L.C.

(57) ABSTRACT

A new and distinct variety of *Gardenia jasminoides* plant named 'Leeone', characterized by its dense, upright, globose growth habit, dark green foliage color, and abundance of fragrant, double white flowers is disclosed.

1 Drawing Sheet

Genus species: *Gardenia jasminoides.*
Varietal denomination: 'Leeone'.

FIELD OF INVENTION

The present invention relates to a new and distinct variety of the genus *Gardenia* and a member of the Rubiaceae family. This new *Gardenia* variety, hereinafter referred to as 'Leeone', was discovered by Robert Edward Lee in October, 2000. 'Leeone' is characterized by its dense, upright, globose growth habit, dark green foliage color, and abundance of fragrant, double white flowers.

BACKGROUND OF THE INVENTION

'Leeone' was found as an openly pollinated seedling in a group of *Gardenia jasminoides* 'Daisy' (unpatented) seedling plants being grown in Independence, La. The value of this new cultivar lies in its dense, upright, globose growth habit, dark green foliage color, and abundance of fragrant, double, white flowers. 'Leeone' has retained many of the outstanding attributes of its parent variety, in particular its tolerance of heat and disease, which makes it adaptable to culture in most of the Sunbelt States. As with the parent variety, the plant of this invention may be advantageously employed as a specimen appointment, in either formal or informal groupings, and is quite attractive in mass plantings. 'Leeone' serves well in foundation plantings and is adaptable for culture as a potted plant. 'Leeone' is responsive to pruning and training and may be maintained without an excessive amount of care. This plant is easy to care for and maintain in size due to its heavy branching and dense canopy. Its natural propensity to remain small to maturity makes it valuable for landscape uses in smaller home gardens which require plants that do not outgrow their intended mature dimensions.

Asexual propagation of the new plant by cuttings has been under Mr. Lee's direction and control in Independence, La. The new plant retains its distinctive characteristics and reproduces true to type in successive generations of asexual reproduction. The plant cannot be reproduced true from seed.

SUMMARY OF THE INVENTION

The following are the most outstanding and distinguishing characteristics of this new cultivar when grown under normal horticultural practices in Independence, La.

1. Dense, upright, and globose in nature.
2. Attractive dark green foliage.
3. The flowers are double, white, fragrant, and profuse.
4. Fast growth rate under normal fertilization and moisture conditions.
5. Hardy to Zone 7.
6. Tolerates full sun to part shade.
7. Heat tolerant.
8. Adaptable to a wide range of soil types.
9. Easily propagated with semi-hardwood cuttings in late spring through the summer.
10. Requires little pruning but is tolerant if pruning is needed.
11. Relatively pest resistant.
12. Good specimen plant.
13. Good foundation plant.
14. Very desirable in planters.

DESCRIPTION OF THE DRAWINGS

This new *Gardenia jasminoides* cultivar is illustrated by the accompanying photographic prints in which.

Figure 1:
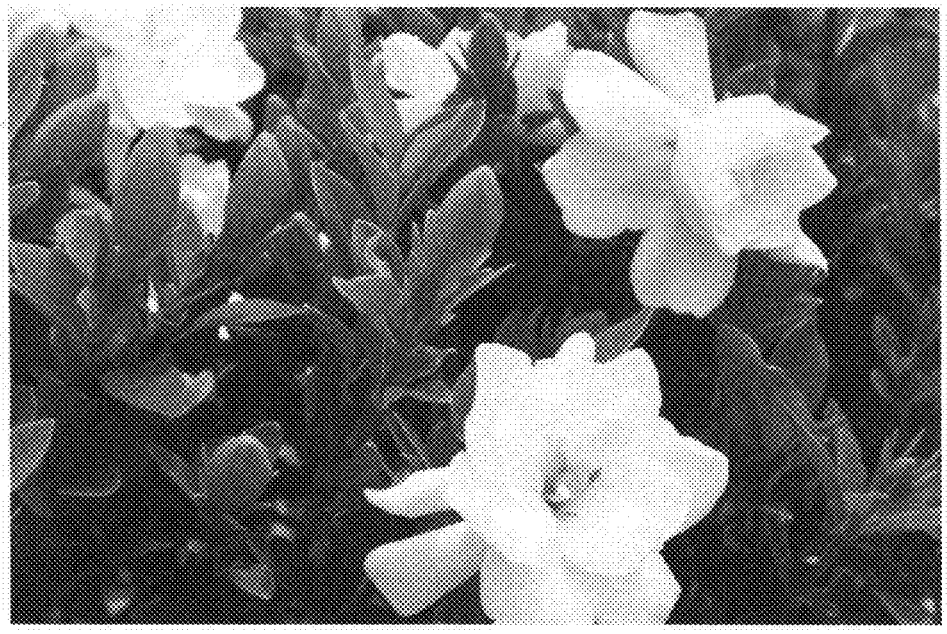
FIG. 1 is a photograph of a close-up showing the flower, buds, foliage and stem color, as well as flower size and form of the new *Gardenia jasminoides* cultivar of the present invention.
Figure 2:
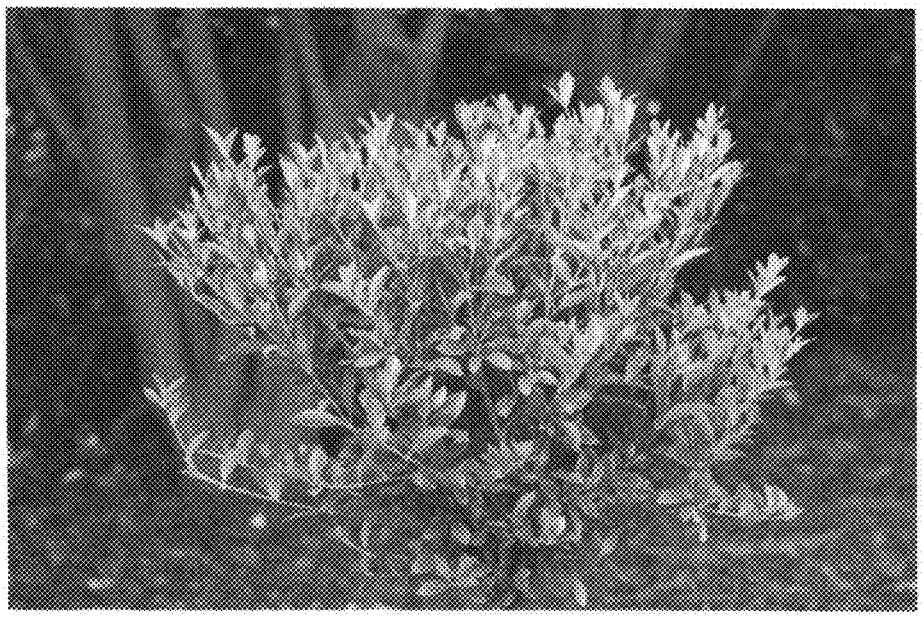
FIG. 2 is a photograph showing the dense, upright, and globose growth habit of a three gallon plant of the new *Gardenia jasminoides* cultivar of the present invention.

The colors shown are as true as is reasonably possible to obtain by conventional photographic procedures. Colors in the photographs may appear different than actual colors due to light reflectance. The colors of the various plant parts are defined with reference to The Royal Horticultural Society Colour Chart. Description of colors in ordinary terms are presented where appropriate for clarity in meaning.

BOTANICAL DESCRIPTION OF THE PLANT

The following is a detailed description of the new variety of *Gardenia* based on observations made of two year old plants grown in one to three gallon containers in commercial production practices, in greenhouses, and in established landscape plantings in Independence, La. and including a comparison with *Gardenia jasminoides* 'Daisy' (unpatented) and *Gardenia jasminoides* 'August Beauty' (unpatented).

DISTINCTIVE CHARACTERISTICS

TABLE 1

| Characteristic | *Gardenia j.* 'Leeone' | *Gardenia j.* 'Daisy' | *Gardenia j.* 'August Beauty' |
|---|---|---|---|
| Height (Mature) | 3-4' (0.9-1.2 m) | 3-3 ½' (0.9-1.05 m) | 4-6' (1.2-1.8 m) |
| Width (Mature) | 2½-3' (0.75-0.9 m) | 3-3½' (0.9-1.05 m) | 4-6' (1.2-1.8 m) |
| Leaf Length | 1½-2¾" (3.8-7 cm) | 1¼-2¼" (3.1-5.7 cm) | 1⅜-3" (4.1-7.5 cm) |
| Leaf Width | ⅝-1⅛" (1.6-2.9 cm) | ⅝-13/16" (1.6-1.9 cm) | ¾-1¼" (1.9-3.1 cm) |
| Leaf Shape | Elliptic-lanceolate | Ovate-rounded | Ovate |
| Growth Habit | Dense, Upright, Globose | Dense, Globose | Dense, Globose |
| Flower Form | Double | Single | Double |
| Bloom Period | May-November | May-July | May-October |

*Gardenia jasminoides* 'Daisy' and *Gardenia jasminoides* 'August Beauty' are well known in the industry and are comparable to 'Leeone' in that all have green foliage color and white fragrant blooms. However, there are many differences. The growth habit of 'Leeone' is dense, upright and globose to 4' (1.2 m) tall compared to 'August Beauty' which is a much taller grower with a more globose habit. The flower form of 'Leeone' is double compared to 'Daisy', the parent variety, which is single. The foliage of 'Leeone' is slightly larger than the parent variety but smaller than 'August Beauty'.

Classification:

Botanical: *Gardenia jasminoides* 'Leeone'

Parentage: Openly pollinated seedling of *Gardenia jasminoides* 'Daisy'

Commercial: Broadleaf evergreen

Form: Dense, upright, and globose

Height: 3-4' (0.9-1.2 m)

Width: 2½-3' (0.75-0.9 m)

Growth Rate: Fast under normal fertilization and moisture conditions. Semi-hardwood cuttings taken in late spring and through the summer produce rooted cuttings in three to four months in Independence, La. Root development is vigorous and finely branched. In a period of four years from a rooted cutting, the plant reaches a height of 2 feet (0.6 m) and a spread of 1½ feet (0.45 m) under normal growing conditions in Independence, La. The plant normally grows at the rate of about 8 inches (20 cm) or more per year and reaches a height of 4 feet (1.2 m) and a spread of 3 feet (0.9 m) at maturity while maintaining a dense habit due to the abundant branch development.

Foliage: Opposite, occasionally in whorls of three, simple, evergreen, glabrous, elliptic to lanceolate and varying in size from 1½" (3.8 cm) to 2¾" (6.9 cm) long and ⅝" (1.6 cm) to 1⅛" (2.9 cm) wide. The petioles are 1/16" (0.2 cm) to ⅛" (0.3 cm) long, 1/32" (0.08 cm) in diameter and Yellow-Green Group 144A. The venation pattern is pinnate. The base of the leaf is cuneate, the margin entire, and the apex acute to short acuminate. The upper surface of the immature leaf is Green Group 137A and the underside is Green Group 138B. Immature midribs and veins are Yellow-Green Group 144B top and bottom and mature to Yellow-Green Group 144A. The upper surface of the mature leaf is Green Group 139A and the underside is Green Group 138A. These mature leaf colors are persistent throughout the winter.

In 2007, the date of initial spring growth was March 20, in Independence, La. After the initial spring flush there was almost continuous growth until fall, ending October 28, also in Independence, La. When grown in full sun, the internode length of this plant is 1¾" (4.4 cm) to 2½" (6.3 cm). When grown in light shade the internode length is 2⅛" (5.4 cm) to 2¾" (6.9 cm). As would be expected, a plant grown in the shade results in a taller, less dense plant with larger leaves.

Stems: The young stems are Yellow-Green Group 144A and tomentulose. As the stems mature they become Yellow-Green Group 146B and by the second growing season they become scaly and Brown Group 200C. The pith is solid and uniform. Young and older stems are densely branched.

Buds: Tubular, bulging at mid-length and tapered to a rounded point, glabrous, 1½" (3.8 cm) to 1¾" (4.4 cm) long by 7/16" (1.1 cm) to 9/16" (1.4 cm) wide and Yellow-Green Group 144B. The pedicel is ½" (1.3 cm) to ⅝" (1.6 cm) long, lightly pubescent and Yellow-Green Group 144A. The calyx is 1⅛" (2.9 cm) to 1 ¼" (3.1 cm) long and ⅝" (1.6 cm) to ¾" (1.9 cm) in diameter, lightly pubescent and Yellow-Green Group 144A. There are 4 to 6 sepals which are Yellow-Green Group 144A, lightly pubescent, linear and joined at the base to form a cup.

Flowers: Perfect, double, glabrous, salverform, 2½" (6.3 cm) to 3" (7.5 cm) in diameter by 1½" (3.8 cm) to 2" (5.0 cm) in depth, borne on current season's growth, fragrant; they last on the plant in the garden five to six days. Flower color is White Group 155D fading to Yellow Group 10D. These color designations are for both the upper surface and the under surface. There are six true petals which are fused at the base, elliptic to obovate, and have wavy margins. These true petals extend radially, are ¾" (1.9 cm) to 1¼" (3.1 cm) long, ⅝" (1.6 cm) to 1⅛" (2.9 cm) wide, have rounded apexes and entire margins. There are 16-18 petaloids ½" (1.3 cm) to 1" (2.5 cm) long and ⅜" (0.9 cm) to ⅞" (2.2 cm) wide which are held more erect and become progressively smaller toward the center producing the double flower. There are six stamens. The anthers are ¼" (0.6 cm) to ⅜" (0.9 cm) long by 1/16" (0.2 cm) wide and Grey-Brown Group 199B. There is no filament structure. Pollen matures to Yellow Group 2D and is produced in small amounts. The pistil is single, non-petaloid, 9/16" (1.4 cm) to 1" (2.5 cm) long and Greyed-Yellow Group 160A. The stigma is ¼" (0.6 cm) to ⅜" (0.9 cm) long, ⅛" (0.3 cm) to 3/16" (0.5 cm) wide in the form of 2-5 enlarged lobes which separate with advanced maturity and are Yellow Group 8C. The style is ⅛" (0.3 cm) to ⅜" (0.9 cm) long, 1/32" (0.08 cm) to 1/16" (0.2 cm) wide and Yellow Group 8D. The ovary is inferior, elliptoid, 3/16" (0.5 cm) to ¼" (0.6 cm) long, ⅛" (0.3 cm) to 3/16" (0.5 cm) wide and Yellow-Green Group 144D.

Culture: Grows well in a wide range of conditions and tolerates sun to part shade. Prefers a moist, well-drained soil that is rich in organic matter. Responds well to mulching and medium applications of fertilizer; prefers pH 5 to 5.5. Very little pruning is needed. Adaptable to containers and above ground planters. Makes a good foundation plant hedge with excellent foliage and flower contrast. Ideal for coastal regions and warmer parts of the Piedmont. Cold hardiness and drought resistance are comparable to the parent variety. Propagated with semi-hardwood cuttings in late spring through the summer.

Disease and Insect Resistance: Resistance to disease and insects common to plants of *Gardenia* has not been observed.

The exemplary embodiments herein disclosed are not intended to be exhaustive or to unnecessarily limit the scope of the invention. The exemplary embodiments were chosen and described in order to explain the present invention so that others skilled in the art may practice the invention.

It is claimed:

1. A new and distinct variety of *Gardenia jasminoides* plant named 'Leeone' as illustrated and described herein.

* * * * *